(12) United States Patent
Decker et al.

(10) Patent No.: US 8,124,391 B2
(45) Date of Patent: Feb. 28, 2012

(54) **THERMOSTABLE POLYMERASES FROM *THERMOCOCCUS PACIFICUS***

(75) Inventors: Katja Decker, Olten (CH); Dirk Löffert, Düsseldorf (DE); Jie Kang, Mettmann (DE)

(73) Assignee: Qiagen GmbH, Hilden (DE)

( * ) Notice: Subject to any disclaimer, the term of this patent is extended or adjusted under 35 U.S.C. 154(b) by 485 days.

(21) Appl. No.: 10/398,011

(22) PCT Filed: Oct. 5, 2001

(86) PCT No.: PCT/EP01/11529
§ 371 (c)(1),
(2), (4) Date: Oct. 3, 2003

(87) PCT Pub. No.: WO02/29016
PCT Pub. Date: Apr. 11, 2002

(65) Prior Publication Data
US 2004/0053279 A1    Mar. 18, 2004

(51) Int. Cl.
*C12N 9/12*    (2006.01)
(52) U.S. Cl. ....... 435/194; 435/183; 536/23.1; 424/94.5
(58) Field of Classification Search .................. 435/194
See application file for complete search history.

(56) References Cited

U.S. PATENT DOCUMENTS
4,683,195 A    7/1987    Mullis et al.
(Continued)

FOREIGN PATENT DOCUMENTS
EP    0 712 927 A2    5/1996
(Continued)

OTHER PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492-495.*

(Continued)

*Primary Examiner* — Richard Hutson
(74) *Attorney, Agent, or Firm* — Fanelli Haag PLLC (57) ABSTRACT

The invention relates to a thermostable polymerase based on *thermococcus pacificus*; DNA molecules which code for one such polymerase; expression vectors; host cells; methods for producing one such polymerase and the use thereof for polymerising nucleic acid, especially in the polymerase chain reaction.

2 Claims, 3 Drawing Sheets

U.S. PATENT DOCUMENTS

| | | | | |
|---|---|---|---|---|
| 4,683,202 | A | | 7/1987 | Mullis |
| 4,800,159 | A | | 1/1989 | Mullis et al. |
| 4,889,818 | A | * | 12/1989 | Gelfand et al. ............... 435/194 |
| 4,965,188 | A | | 10/1990 | Mullis et al. |
| 5,023,171 | A | | 6/1991 | Ho et al. |
| 5,066,584 | A | | 11/1991 | Gyllensten et al. |
| 5,075,216 | A | | 12/1991 | Innis et al. |
| 5,079,352 | A | | 1/1992 | Gelfand et al. |
| 5,091,310 | A | | 2/1992 | Innis |
| 5,104,792 | A | | 4/1992 | Silver et al. |
| 5,210,036 | A | * | 5/1993 | Comb et al. ................. 435/194 |
| 5,242,818 | A | * | 9/1993 | Oshima et al. ............... 435/194 |
| 5,436,149 | A | | 7/1995 | Barnes |
| 5,491,086 | A | | 2/1996 | Gelfand et al. |
| 5,545,552 | A | | 8/1996 | Mathur |
| 5,602,011 | A | | 2/1997 | Luhm et al. |
| 6,008,025 | A | * | 12/1999 | Komatsubara et al. ...... 435/91.2 |
| 6,228,628 | B1 | | 5/2001 | Gelfand et al. |
| 6,555,357 | B1 | | 4/2003 | Kaiser et al. |
| 6,607,883 | B1 | | 8/2003 | Frey et al. |
| 6,627,424 | B1 | | 9/2003 | Wang |
| 7,425,423 | B1 | * | 9/2008 | Ankenbauer et al. .......... 435/15 |
| 2003/0228616 | A1 | | 12/2003 | Arezi et al. |
| 2004/0053279 | A1 | | 3/2004 | Decker et al. |

FOREIGN PATENT DOCUMENTS

| | | | |
|---|---|---|---|
| EP | 0 745 675 | | 12/1996 |
| EP | 0 834 570 | A1 | 4/1998 |
| EP | 0 892 058 | A2 | 1/1999 |
| EP | 834570 | * | 10/1999 |
| GB | 2 344 591 | A | 6/2000 |
| JP | 1997252776 | | 9/1997 |
| WO | WO 92/06200 | | 4/1992 |
| WO | WO 96/10640 | | 4/1996 |
| WO | WO 97/29209 | | 8/1997 |
| WO | WO 98/14590 | | 4/1998 |
| WO | WO 98/49274 | | 11/1998 |
| WO | WO 99/47649 | | 9/1999 |
| WO | WO 01/18213 | A1 | 3/2001 |
| WO | WO 01/61015 | | 8/2001 |
| WO | WO 02/29016 | A2 | 4/2002 |

OTHER PUBLICATIONS

Hopfner et al., *Proceedings of the National Academy for Sciences of USA*, 96(7): 3600-3605 (1999).

Miroshnichenko et al., *Int. J. Syst. Bacteriol.*, 48: 23-29 (1998).

Accession No. Y16226; GI:3059149, *Thermococcus gorgonarius* 16S rRNA gene, Apr. 15, 1998.

Accession No. Y16227; *Thermococcus pacificus* 16S rRNA gene, Apr. 15, 1998.

Ogata et al., Nucleic Acids Research, 1998, vol. 26, No. 20, pp. 4652-4656.

Ogata et al., Biochem. J. (1997), 324, 667-671.

Mattila et al., Nucleic Acids Research, 1991, vol. 19, No. 18, pp. 4967-4973.

Kong et al., Journal of Biological Chemistry, 1993, vol. 268, No. 3, Issue of Jan. 25, pp. 1965-1975.

Keohavong et al., PCR Methods and Applications, 2:288-292.

Cariello et al., 1991, Nucleic Acids Research, vol. 19, No. 15 4193-4198.

Accession No. 1TGO_A; GI:4699806, Chain A, Thermostable B Type Dna Polymerase From *Thermococcus*; Jul. 10, 2009.

Hopfner et al., Proc Natl Acad Sci U S A. Mar. 30, 1999;96(7):3600-5.

Abramson, "Chapter 4: Thermostable DNA Polymerases", PCR Strategies (1995), Academic Press, Inc., pp. 39-57.

Akhmetzjanov and Vakhitov, "Molecular cloning and nucleotide sequence of the DNA polymerase gene from *Thermus flavus*", Nucleic Acids Research, vol. 20 (1992), p. 5839.

Asakura et al., "Cloning, Nucleotide Sequence, and Expression in *Escherichia coli* of DNA Polymerase Gene (poIA) from *Thermus thermophilus* HB8", Journal of Fermentation and Bioengineering, vol. 76 (1993), pp. 265-269.

Barnes, "PCR amplification of up to 35-kb DNA with high fidelity and high yield from bacteriophage templates", Proc. Natl. Acad. Sci. USA, vol. 91 (1994), pp. 2216-2220.

Bernard et al., "A Conserved 3'→5' Exonuclease Active Site in Prokaryotic and Eukaryotic DNA Polymerases", Cell, vol. 59 (1989), pp. 219-228.

Cann et al., "Two Family B DNA Polymerases from *Aeropyrum pernix*, an Aerobic Hyperthermophilic Crenarchaeote", Journal of Bacteriology, vol. 181 (1999), pp. 5984-5992.

Dabrowski and Kur, "Cloning and Expression in *Escherichia coli* of the Recombinant His-Tagged DNA Polymerases from *Pyrococcus furiosus* and *Pyrococcus woesei*", Protein Expression and Purification, vol. 14 (1998), pp. 131-138.

Datukishvili et al., "The DNA polymerase-encoding gene from a thermoacidophilic archaeon *Sulfolobus acidocaldarius*", Gene, vol. 177 (1996), pp. 271-273.

Edgell et al., "Gene Duplications in Evolution of Archaeal Family B DNA Polymerases", Journal of Bacteriology, vol. 179 (1997), pp. 2632-2640.

Eom et al., "Structure of Taq polymerase with DNA at the polymerase active site", Nature, vol. 382 (1996), pp. 278-281.

Flaman et al., "A rapid PCR fidelity assay", Nucleic Acids Research, vol. 22 (1994), pp. 3259-3260.

Huang and Ito, "The hyperthermophilic bacterium *Thermotoga maritime* has two different classes of family C DNA polymerases: evolutionary implications", Nucleic Acids Research, vol. 26 (1998), pp. 5300-5309.

Jacobsen et al., "The N-Terminal Amino-Acid Sequences of DNA Polymerase I from *Escherichia coli* and of the Large and the Small Fragments Obtained by a Limited Proteolysis", Eur. J Biochem., vol. 45 (1974), pp. 623-627.

Joyce and Grindley, "Construction of a plasmid that overproduces the large proteolytic fragment (Klenow fragment) of DNA polymerase I of *Escherichia coli*", Proc. Natl. Acad. Sci. USA, vol. 80 (1983), pp. 1830-1834.

Joyce and Steitz, "Function and Structure Relationships in DNA Polymerases", Annu. Rev. Biochem., vol. 63 (1994), pp. 777-822.

Jung et al., "Cloning and Analysis of the DNA Polymerase-encoding Gene from *Thermus filiformis*", Mol. Cells, vol. 7 (1997), pp. 769-776.

Kahler and Antranikian, "Cloning and Characterization of a Family B DNA Polymerase from the Hyperthermophilic Crenarchaeon *Pyrobaculum islandicum*", Journal of Bacteriology, vol. 182 (2000), pp. 655-663.

Kawarabayasi et al., "Complete Sequence and Gene Organization of the Genome of a Hyperthermophilic Archaebacterium, *Pyrococcus horikoshii* OT3", DNA Research, vol. 5 (1998), pp. 55-76.

Kawarabayasi et al., EMBL Data Library Accession No. C75023, Dec. 15, 1998.

Kiefer et al., "Crystal structure of a thermostable *Bacillus* DNA polymerase I large fragment at 2.1 A resolution", Structure, vol. 5 (1997), pp. 95-108.

Klenow and Henningsen, "Selective Elimination of the Exonuclease Activity of the Deoxyribonucleic Acid Polymerase from *Escherichia coli* B by Limited Proteolysis", Proceedings of the National Academy of Sciences, vol. 65 (1970), pp. 168-175.

Lawyer et al., "Isolation, Characterization, and Expression in *Escherichia coli* of the DNA Polymerase Gene from *Thermus aquaticus*", The Journal of Biological Chemistry, vol. 264 (1989), pp. 6427-6437.

Loffert et al., U.S.P.T.O. Office Action, U.S. Appl. No. 10/216,682, Feb. 19, 2010, 9 pgs.

Loffert et al., U.S.P.T.O. Office Action, U.S. Appl. No. 10/216,682, Jul. 31, 2009, 25 pgs.

Loffert et al., U.S.P.T.O. Office Action, U.S. Appl. No. 10/216,682, Jun. 25, 2007, 14 pgs.

Loffert et al., U.S.P.T.O. Office Action, U.S. Appl. No. 10/216,682, Jan. 24, 2006, 12 pgs.

Loffert et al., U.S.P.T.O. Office Action, U.S. Appl. No. 10/216,682, Apr. 5, 2004, 12 pgs.

Loffert et al., U.S.P.T.O. Office Action, U.S. Appl. No. 10/216,682, Apr. 9, 2008, 16 pgs.

Loffert et al., U.S.P.T.O. Office Action, U.S. Appl. No. 10/216,682, Aug. 4, 2006, 6 pgs.

Loffert et al., U.S.P.T.O. Office Action, U.S. Appl. No. 10/216,682, Dec. 28, 2004, 7 pgs.

Loffert et al., U.S.P.T.O. Requirement for Restriction/Election, U.S. Appl. No. 10/216,682, Jan. 21, 2004, 6 pgs.

Longley et al., "Characterization of the 5' to 3' exonuclease associated with *Thermus aquaticus* DNA polymerase", Nucleic Acids Research, vol. 18 (1990), pp. 7317-7322.

Mendelman et al., "Base Mispair Extension Kinetics", The Journal of Biological Chemistry, vol. 265 (1990), pp. 2338-2346.

Perler et al., "Intervening sequences in an Archaea DNA polymerase gene", Proc. Natl. Acad. Sci. USA, vol. 89 (1992), pp. 5577-5581.

Petruska et al., "Comparison between DNA melting thermodynamics and DNA polymerase fidelity", Proc. Natl. Acad. Sci. USA, vol. 85 (1988), pp. 6252-6256.

Pisani et al., "A DNA polymerase from the archaeon *Sulfolobus solfataricus* shows sequence similarity to family B DNA polymerase", Nucleic Acids Research, vol. 20 (1992), pp. 2711-2716.

Pisani et al., "Domain organization and biochemical features of *Sulfolobus solfataricus* DNA polymerase", Extremophiles, vol. 2 (1998), pp. 171-177.

Pisani et al., EMBL Data Library Accession No. S23019, Jan. 13, 1995.

Prangishvili and Klenk, "Nucleotide sequence of the gene for a 74 kDa DNA polymerase from the archaeon *Sulfolobus solfataricus*", Nucleic Acids Research, vol. 21 (1993), p. 2768.

Southworth et al., "Cloning of thermostable DNA polymerases from hyperthermophilic marine Archaea with emphasis on *Thermococcus* sp. 9°N-7 and mutations affecting 3'-5' exonuclease activity", Proc. Natl. Acad. Sci. USA, vol. 93 (1996), pp. 5281-5285.

Tagaki et al., "Characterization of DNA Polymerase from *Pyrococcus* sp. Strain KOD1 and Its Application to PCR", Applied and Environmental Microbiology, vol. 63 (1997), pp. 4504-4510.

Uemori et al., "Organization and nucleotide sequence of the DNA polymerase gene from the archaeon *Pyrococcus furiosus*", Nucleic Acids Research, vol. 21 (1993), pp. 259-265.

Uemori et al., "The Hyperthermophilic Archaeon *Pyrodictium occultum* Has Two a-Like DNA Polymerases", Journal of Bacteriology, vol. 177 (1995), pp. 2164-2177.

Williams et al., "DNA Relatedness of *Thermus* Strains, Description of *Thermus brockianus* sp. nov., and Proposal to Reestablish *Thermus thermophilus* (Oshima and Imahori)", International Journal of Systematic Bacteriology, vol. 45 (1995), pp. 495-499.

Usui et al., "Small Heat Shock Protein of a Hyperthermophilic Archaeum, *Thermococcus* sp. Strain KS-1, Exists as a Spherical 24 mer and Its Expression Is Highly Induced under Heat-Stress Conditions", Journal of Bioscience and Bioengineering, vol. 92, No. 2 (2001), pp. 161-166.

Fujiwara, et al., "Expression Profiles and Physiological Roles of Two Types of Molecular Chaperonins from the Hyperthermophilic Archaeon *Thermococcus kodakarensis*", Applied and Environment Microbilogy, vol. 74, No. 23 (2008), pp. 7306-7312.

* cited by examiner

SEQUENCE LISTING

```
<160> NUMBER OF SEQ ID NOS: 7

<210> SEQ ID NO 1
<211> LENGTH: 2322
<212> TYPE: DNA
<213> ORGANISM: Thermococcus pacificus

<400> SEQUENCE: 1
atgatcctcg atgccgacta cattaccgaa gacggaaagc ccgtcatcag gatattcagg      60
aaggagaagg gcgagtttaa gatcgagtac gacaggaatt ttgagcccta cttctatgcc     120
ctcctgaagg acgattctgc gattgaagac gtcaaaaaga taaccgcgga gaggcacggc     180
actaccgtta gggtcgtcag ggccgagaag gtgaagaaga agttcctcgg caggccgata     240
gaggtctgga agctctactt cacccacccc caggacgttc ccgcaatcag agacaaaata     300
agggaacatc cagccgttgt ggacatctac gagtacgaca tccccttcgc gaagcgctac     360
ctcatagaca agggcttaat cccgatggag ggcgatgaag aacttaagat gctcgccttc     420
gacatcgaga cgctctacca cgagggcgag gagttcgccg aagggcccat cctgatgata     480
agctacgccg acgaggaagg ggcgcgcgtt attacctgga agaatatcga cctcccctac     540
gttgacgtcg tttccactga gaaggagatg ataaagcgct tcctcagggt catcaaggag     600
```

-continued

```
aaggatcccg acgtgctaat aacatacaac ggcgataact tcgacttcgc ctacctcaag    660
aagcgctccg agaagctcgg cgtcaagttc atcctcggga gggacggcag tgagccgaaa    720
attcagagga tgggcgaccg ctttgcagtg gaggtcaagg gaaggattca cttcgacctc    780
taccccgtca taaggaggac gattaacctg cccacttaca cccttgaggc agtatatgaa    840
gccatctttg gacagccaaa ggagaaggtc tacgcggaag agataacgca ggcctgggag    900
acgggcgagg gattagaaag ggtggcccgc tactcgatgg aagatgctaa ggtaacctac    960
gagctcggaa aagagttctt cccgatggag gcccagctct cgcgtctcgt aggccagagc   1020
ctctgggatg tctcgcgctc gagtaccgga acctcgtcg agtggttttt gctgaggaag    1080
gcctacgaga ggaacgagct tgcaccaaac aagccagacg agaaggaact ggccaggaga   1140
agggagagct acgcgggtgg atacgtcaag gagcctgaga aaggactgtg gaaaacata   1200 gtctacttag attttcgctc tctctacccc tctataatta ttacacacaa cgtctcccca   1260
gatacgctca acagggaggg ctgtaaggag tacgacgtgg ctcctcaggt gggacaccgc   1320
ttctgcaagg acttccccgg cttcattccg agcctcctcg agaccttttt ggaggagagg   1380
cagaagataa agaagaacat gaaggccacg atagacccga tcgagaagaa gctccttgat   1440
tacaggcaac gggccattaa aatccttgct aatagtttct acggttacta cggctacgca   1500
aaggcccgct ggtactgcag ggagtgcgcc gagagcgtga cagcttgggg caggcagtac   1560
atcgagacca cgataaggga aatagaggat aaatttggct ttaaagtgct ttacgcagac   1620
accgacgggt ttttcgcgac aatcccagga gctgatgccg aaaccgtcaa aaagaagtcc   1680
aaggagttcc tcaagtatat taacgccaag ctgcccggcc tgctcgagct ggagtacgag   1740
ggcttctaca gcgcggtttt cttcgtgacg aagaagaagt acgcggttat agacgaggaa   1800
gacaagataa cgacgcgcgg gcttgaaata gtcaggcgtg actggagcga gatagcaaag   1860
gagacgcagg cgagggttct tgaggcgata ctcaagcacg gtgacgttga ggaagctgta   1920
aagattgtca aagaggtgac ggaaaagctc agcaagtacg aagttccacc agagaagctt   1980
gtcatccacg agcagataac tcgcgacctg aaggactaca aggccaccgg cccgcatgtg   2040
gctgttgcaa agcgcctcgc cgcgagggga ataaaaatcc ggcccgggac ggtcataagc   2100
tacatcgtgc tcaaaggctc tggaaggatt ggggacaggg ctataccgtt cgacgagttc   2160
gatccgacaa agcacaagta cgatgcggaa tactacatcg agaaccaggt tctgccggcg   2220
gtggagagaa ttctgagggc ctttggctac cgtaaggagg acctacgcta ccagaagacg   2280
cggcaggttg gcttgggggc gtggctaaaa cctaagacat ga                      2322
```

<210> SEQ ID NO 2
<211> LENGTH: 773
<212> TYPE: PRT
<213> ORGANISM: Thermococcus pacificus

<400> SEQUENCE: 2

Met Ile Leu Asp Ala Asp Tyr Ile Thr Glu Asp Gly Lys Pro Val Ile
1               5                   10                  15

Arg Ile Phe Arg Lys Glu Lys Gly Glu Phe Lys Ile Glu Tyr Asp Arg
            20                  25                  30

Asn Phe Glu Pro Tyr Phe Tyr Ala Leu Leu Lys Asp Asp Ser Ala Ile
        35                  40                  45

Glu Asp Val Lys Lys Ile Thr Ala Glu Arg His Gly Thr Thr Val Arg
    50                  55                  60

Val Val Arg Ala Glu Lys Val Lys Lys Lys Phe Leu Gly Arg Pro Ile
65                  70                  75                  80

```
Glu Val Trp Lys Leu Tyr Phe Thr His Pro Gln Asp Val Pro Ala Ile
            85                  90                  95

Arg Asp Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
            115                 120                 125

Met Glu Gly Asp Glu Glu Leu Lys Met Leu Ala Phe Asp Ile Glu Thr
    130                 135                 140

Leu Tyr His Glu Gly Glu Glu Phe Ala Glu Gly Pro Ile Leu Met Ile
145                 150                 155                 160

Ser Tyr Ala Asp Glu Glu Gly Ala Arg Val Ile Thr Trp Lys Asn Ile
                165                 170                 175

Asp Leu Pro Tyr Val Asp Val Val Ser Thr Glu Lys Glu Met Ile Lys
            180                 185                 190

Arg Phe Leu Arg Val Ile Lys Glu Lys Asp Pro Asp Val Leu Ile Thr
        195                 200                 205

Tyr Asn Gly Asp Asn Phe Asp Phe Ala Tyr Leu Lys Lys Arg Ser Glu
    210                 215                 220

Lys Leu Gly Val Lys Phe Ile Leu Gly Arg Asp Gly Ser Glu Pro Lys
225                 230                 235                 240

Ile Gln Arg Met Gly Asp Arg Phe Ala Val Glu Val Lys Gly Arg Ile
                245                 250                 255

His Phe Asp Leu Tyr Pro Val Ile Arg Arg Thr Ile Asn Leu Pro Thr
            260                 265                 270

Tyr Thr Leu Glu Ala Val Tyr Glu Ala Ile Phe Gly Gln Pro Lys Glu
        275                 280                 285

Lys Val Tyr Ala Glu Glu Ile Thr Gln Ala Trp Glu Thr Gly Glu Gly
    290                 295                 300

Leu Glu Arg Val Ala Arg Tyr Ser Met Glu Asp Ala Lys Val Thr Tyr
305                 310                 315                 320

Glu Leu Gly Lys Glu Phe Phe Pro Met Glu Ala Gln Leu Ser Arg Leu
                325                 330                 335

Val Gly Gln Ser Leu Trp Asp Val Ser Arg Ser Ser Thr Gly Asn Leu
            340                 345                 350

Val Glu Trp Phe Leu Leu Arg Lys Ala Tyr Glu Arg Asn Glu Leu Ala
        355                 360                 365

Pro Asn Lys Pro Asp Glu Lys Glu Leu Ala Arg Arg Arg Glu Ser Tyr
    370                 375                 380

Ala Gly Gly Tyr Val Lys Glu Pro Glu Lys Gly Leu Trp Glu Asn Ile
385                 390                 395                 400

Val Tyr Leu Asp Phe Arg Ser Leu Tyr Pro Ser Ile Ile Ile Thr His
                405                 410                 415

Asn Val Ser Pro Asp Thr Leu Asn Arg Glu Gly Cys Lys Glu Tyr Asp
            420                 425                 430

Val Ala Pro Gln Val Gly His Arg Phe Cys Lys Asp Phe Pro Gly Phe
        435                 440                 445

Ile Pro Ser Leu Leu Gly Asp Leu Leu Glu Glu Arg Gln Lys Ile Lys
    450                 455                 460

Lys Asn Met Lys Ala Thr Ile Asp Pro Ile Glu Lys Lys Leu Leu Asp
465                 470                 475                 480

Tyr Arg Gln Arg Ala Ile Lys Ile Leu Ala Asn Ser Phe Tyr Gly Tyr
                485                 490                 495

Tyr Gly Tyr Ala Lys Ala Arg Trp Tyr Cys Arg Glu Cys Ala Glu Ser
```

```
                    500                 505                 510
Val Thr Ala Trp Gly Arg Gln Tyr Ile Glu Thr Thr Ile Arg Glu Ile
        515                 520                 525

Glu Asp Lys Phe Gly Phe Lys Val Leu Tyr Ala Asp Thr Asp Gly Phe
    530                 535                 540

Phe Ala Thr Ile Pro Gly Ala Asp Ala Glu Thr Val Lys Lys Lys Ser
545                 550                 555                 560

Lys Glu Phe Leu Lys Tyr Ile Asn Ala Lys Leu Pro Gly Leu Leu Glu
                565                 570                 575

Leu Glu Tyr Glu Gly Phe Tyr Lys Arg Gly Phe Phe Val Thr Lys Lys
                580                 585                 590

Lys Tyr Ala Val Ile Asp Glu Glu Asp Lys Ile Thr Thr Arg Gly Leu
                595                 600                 605

Glu Ile Val Arg Arg Asp Trp Ser Glu Ile Ala Lys Glu Thr Gln Ala
                610                 615                 620

Arg Val Leu Glu Ala Ile Leu Lys His Gly Asp Val Glu Glu Ala Val
625                 630                 635                 640

Lys Ile Val Lys Glu Val Thr Glu Lys Leu Ser Lys Tyr Glu Val Pro
                645                 650                 655

Pro Glu Lys Leu Val Ile His Glu Gln Ile Thr Arg Asp Leu Lys Asp
                660                 665                 670

Tyr Lys Ala Thr Gly Pro His Val Ala Val Ala Lys Arg Leu Ala Ala
                675                 680                 685

Arg Gly Ile Lys Ile Arg Pro Gly Thr Val Ile Ser Tyr Ile Val Leu
                690                 695                 700

Lys Gly Ser Gly Arg Ile Gly Asp Arg Ala Ile Pro Phe Asp Glu Phe
705                 710                 715                 720

Asp Pro Thr Lys His Lys Tyr Asp Ala Glu Tyr Tyr Ile Glu Asn Gln
                725                 730                 735

Val Leu Pro Ala Val Glu Arg Ile Leu Arg Ala Phe Gly Tyr Arg Lys
                740                 745                 750

Glu Asp Leu Arg Tyr Gln Lys Thr Arg Gln Val Gly Leu Gly Ala Trp
                755                 760                 765

Leu Lys Pro Lys Thr
                770

<210> SEQ ID NO 3
<211> LENGTH: 21
<212> TYPE: DNA
<213> ORGANISM: artificial
<220> FEATURE:
<223> OTHER INFORMATION: primer

<400> SEQUENCE: 3
atgatcctcg atgccgacta c                                             21

<210> SEQ ID NO 4
<211> LENGTH: 24
<212> TYPE: DNA
<213> ORGANISM: artificial
<220> FEATURE:
<223> OTHER INFORMATION: primer

<400> SEQUENCE: 4
tcatgtctta ggttttagcc acgc                                          24

<210> SEQ ID NO 5
<211> LENGTH: 30
```

```
<212> TYPE: DNA
<213> ORGANISM: artificial
<220> FEATURE:
<223> OTHER INFORMATION: primer

<400> SEQUENCE: 5
tttcccagtc acgacgttgt aaaacgacgg                                          30

<210> SEQ ID NO 6
<211> LENGTH: 19
<212> TYPE: DNA
<213> ORGANISM: artificial
<220> FEATURE:
<223> OTHER INFORMATION: primer

<400> SEQUENCE: 6
gcaccccgct tgggcagag                                                      19

<210> SEQ ID NO 7
<211> LENGTH: 20
<212> TYPE: DNA
<213> ORGANISM: artificial
<220> FEATURE:
<223> OTHER INFORMATION: primer

<400> SEQUENCE: 7
tcccgcccct cctggaagac                                                     20
```

THERMOSTABLE POLYMERASES FROM *THERMOCOCCUS PACIFICUS*

This application is a United States national filing under 35 U.S.C. §371 of international (PCT) application No. PCT/EP01/11529, filed Oct. 5, 2001, designating the US, and claiming priority to German Application No. 100 49 211.8, filed Oct. 5, 2000.

The present invention relates to a thermostable polymerase from *Thermococcus pacificus*, DNA molecules which code for such a polymerase, expression vectors, host cells, process for preparing a polymerase of this kind and the use thereof for the polymerisation of nucleic acid, particularly in the polymerase chain reaction.

DNA polymerases are a family of enzymes which catalyse the polymerisation of nucleic acids and play a part in both DNA replication and in DNA repair. Thermostable DNA polymerases are frequently used in in-vitro processes, for example in the polymerase chain reaction (PCR), which has become an indispensable process in molecular biology. A common problem of the DNA polymerases used for this purpose is the incorporation of the wrong nucleotides during DNA synthesis, which leads to mutated PCR products. This may cause problems in some molecular-biological applications, particularly in the cloning and subsequent recombinant expression of protein, as the mutations introduced may lead to inactive protein or protein which differs from the original protein in its properties. The mis-incorporation may be corrected by polymerases which have an inherent 3'-5'-exonuclease activity (so-called proofreading enzymes). The enzyme most commonly used in PCR, Taq DNA polymerase, does not have this enzymatic activity, and it is known that the error rate of this enzyme is more than ten times higher than that of the proofreading enzymes (U.S. Pat. No. 5,545,552).

Various other known heat-stable DNA polymerases do indeed have a proofreading activity, but have other disadvantages (Lundberg et al. 1991, Gene 108:1-6; EP 0 455 430; EP 0 701 000; WO 92/03556; WO 92/09689). Thermostable DNA polymerases with 3'-5'-exonuclease activity are also known particularly from the organisms *Thermococcus gorgonarius* (WO 98/14590 A1) and the Archaeon strain KOD1 (EP 0 745 675 A2).

There is still a need for new thermostable DNA polymerases with proofreading activity and improved properties with regard to their usefulness in molecular biology, particularly increased heat stability, 3'-5'-exonuclease activity, and proofreading ability under PCR-conditions.

This problem is solved by the provision of a new thermostable DNA polymerase, obtainable from the organism *Thermococcus pacificus*.

The present invention relates particularly to a thermostable DNA polymerase from *Thermococcus pacificus* with 3'-5'-exonuclease activity. Preferably a DNA polymerase of this kind has the amino acid sequence SEQ ID NO: 2 (numerical code <210>2 or <400>2 in the attached sequence listing).

In another aspect the present invention relates to a DNA molecule which codes for a thermostable DNA polymerase with 5'-3'-polymerase activity, and which
  (a) contains the sequence SEQ ID NO: 1 (numerical code <210>1 or <400>1 in the attached sequence listing) or the sequence complementary thereto; or
  (b) contains a sequence which constitutes a coherent fragment of at least 60, preferably at least 90 nucleotides of SEQ ID NO:1 or the sequence complementary thereto; or
  (c) contains a sequence which is so similar to SEQ ID NO: 1 or the sequence complementary thereto that the DNA molecule hybridises under stringent conditions with another DNA molecule which contains SEQ ID NO: 1 or the sequence complementary thereto; or
  (d) contains a sequence which codes for a cohesive fragment of at least 100 amino acids, preferably at least 200 amino acids of the sequence SEQ ID NO: 2.

By stringent conditions are meant for the purposes of the present invention conditions under which two DNA molecules in a hybridisation experiment hybridise with one another if they have a sequence identity of 97% or more, preferably 98% or more, most preferably 99% or more in the hybridising section. The skilled man knows how to achieve such conditions (Sambrook, Fritsch, Maniatis. Molecular Cloning. A Laboratory Manual, 1989. 9.47).

One way of obtaining a DNA molecule according to the invention is to isolate it from the organism *Thermococcus pacificus*. *Thermococcus pacificus* is known in the art (Miroshnichenko et al. 1998, *Thermococcus gorgonarius* sp. nov. and *Thermococcus pacificus* sp. nov.: heterotrophic extremely thermophilic archaea from New Zealand submarine hot vents. Int. J. Syst. Bacteriol. 48:23-29) and obtainable from public collections (DSMZ-Deutsche Sammlung von Mikroorganismen and Zellkulturen GmbH, Mascheroder Weg 1 b, 38124 Braunschweig, German, DSM No. 10394; American Type Culture Collection, 10801 University Boulevard, Manassas, Va. 20110, USA, ATCC 700653).

The organism may be cultivated in a manner known per se. A ready-made medium produced by Messrs Becton Dickinson (Bacto Marine Broth 2216) may be used. The medium may be made up in accordance with the manufacturer's instructions and the DSMZ (media 514 and 760); the addition of sulphur may be omitted, with a slight loss of yield. The medium may be made anaerobic by treatment with $N_2$ gas; this can be checked by adding resazurin (1 mg/l final concentration). In order to cultivate larger volumes of culture, for example, preliminary cultures may be used to begin with. For these, 2 ml of the starting culture obtained from the DSMZ (DSM 10394) may be inoculated onto 20 ml of medium under anaerobic conditions. The incubation may take place overnight at 85° C. without shaking in culture flasks with an airtight seal. To start up the main cultures 20 ml of the preliminary culture may be anaerobically inoculated onto 500 ml of fresh medium and incubated under the same conditions as the preliminary cultures.

The harvesting of the cultures may be done by transferring the cultures into anaerobic centrifuge cups and then centrifuging the samples for 15 min at 4° C. and 4000×g. The cell pellet thus obtained can then be used for the preparation of the genomic DNA by current methods.

The purified genomic DNA can be subject to a PCR reaction for example with the primers SEQ ID NO. 3, ATGATCCTCGATGCCGACTAC (Tpac3') and SEQ ID NO. 4, TCATGTCTTAGGTTTTAGCCACGC (Tpac5'), in which the SEQ ID NO. 1 is amplified. The amplification product can then be purified by standard methods, e.g. with the QIAquick PCR Purification Kit or QIAquick gel Extraction Kit (QIAGEN GmbH, Hilden, Germany).

Another method of producing a DNA molecule of the present invention consists in chemically synthesising such a DNA molecule. To do this, for example, suitable oligonucleotides are first prepared by methods known per se for synthesising oligonucleotides (e.g. Gait, M. J., 1984, *Oligonucleotide Synthesis. A Practical Approach*. IRL Press, Oxford, UK), from which a synthetic gene can be prepared by various methods. Such methods are known in the art (e.g. Stemmer et al. 1995, *Single-step assembly of a gene and entire plasmid from large numbers of oligodeoxyribonucleotides*, Gene 164

(1): 49-53; Ye et al. 1992, *Gene synthesis and expression in E. coli for pump, a human matrix metalloproteinase*, Biochem Biophys Res Commun 186(1):143-9; Hayden et Mandecki 1988, *Gene synthesis by serial cloning of oligonucleotides*, DNA 7(8): 571-7). In this way for example a DNA molecule with the sequence SEQ ID NO: 1 may be prepared by methods known per se.

It is within the capabilities of the average man skilled in the art to prepare DNA molecules which are variants of a DNA molecule with the SEQ ID NO: 1 and similarly code for a thermostable DNA polymerase with essentially unaltered properties. Such variants differ from DNA molecules of SEQ ID NO: 1 in that one, two, three, four, five, six, seven, eight, nine, ten or more nucleotides are deleted or substituted by nucleotides with other bases, or additional nucleotides are inserted or added. By routine experiments the skilled man can determine whether such a modification has a significant influence on the properties of the polypeptide coded by a DNA molecule of this kind. He has no difficulty finding, by routine experiments, a large number of such variants which code for a thermostable DNA polymerase with essentially unaltered properties. Such variants are therefore expressly included in the invention.

Thus, the skilled man can in particular produce variants which are degenerate compared with a DNA molecule with the sequence SEQ ID NO: 1 in terms of the genetic code, i.e. DNA molecules with a nucleotide sequence other than SEQ ID NO: 1, but which code for the same amino acid sequence. This may be useful, when a DNA molecule of this kind is expressed in a host cell, for optimising the codons with regard to the codons of the host cell in question which are preferably used. The skilled man will be aware of such processes.

It is also within the capabilities of the average person skilled in the art to delete smaller or larger sequence fragments, leading during expression to polypeptides with corresponding deletions in the amino acid sequence. Using computer methods known per se based on comparing a sequence, in this case SEQ ID NO: 1, with the sequences of other, well characterised proteins, the skilled man can determine which sequence fragments (domains) are responsible for the enzymatic activities, polymerase or exonuclease activity. Outside these domains in particular deletions (and of course substitutions as well) are possible, which have no major effect on the enzymatic activity. It is easy to tell whether a particular deletion in this sense has no effects.

It is also possible to modify the DNA molecule so that the DNA polymerase according to the invention takes the form of a fusion protein with additional amino acid sequences. Thus for example an affinity marker in the form of a short peptide sequence may be attached to the C-terminus, for example a histidine hexamer which makes it easier to purify the protein (see below).

The skilled man may also deliberately switch off one of the two enzymatic activities by mutation, for example by substitution or deletion of one or more amino acids, or by deletion of an entire sequence fragment in the corresponding domain up to deletion of the entire domain. Thus, for example, the skilled man may prepare a DNA molecule which codes for a polypeptide which has a polymerase, but not an exonuclease activity. This may be advantageous if a polypeptide of this kind is to be used for example in DNA sequencing.

In one particular embodiment, the DNA molecule according to the invention codes for a polypeptide which has both 5'-3'-DNA polymerase and 3'-5'-exonuclease activity.

In another aspect the present invention relates to a vector which contains a DNA molecule according to the invention, particularly an expression vector. Preferably an expression vector of this kind has the following features:
 (a) one or more promoters;
 (b) at least one operator which may be used to increase or suppress gene expression;
 (c) termination sequences for transcription and translation.

In an expression vector of this kind the DNA molecule according to the invention is operatively connected with these features, with the result that the expression vector allows expression of the thermostable DNA polymerase according to the invention in a host cell. Expression vectors which are suitable for such purposes are known in large numbers in the prior art, as are methods of introducing the DNA molecule according to the invention into such a vector, introducing the vector into host cells, cultivating the host cells and isolating the polypeptide formed (cf. e.g. Sambrook et al., Molecular Cloning, $2^{nd}$ Ed., Cold Spring Harbour 1989, particularly Chapter 17). Suitable expression vectors are for example the pQE vectors which may be obtained commercially from Messrs Qiagen GmbH, 40724 Hilden, Germany. These vectors enable an affinity marker, for example a histidine hexamer, to be incorporated at the same time into the polypeptide formed, by means of which the polypeptide can be purified easily and effectively. (Crowe et al., 1994, *6xHis-Ni-NTA chromatography as a superior technique in recombinant protein expression/purification*, Methods Mol Biol. 31:371-87; Stüber et al. 1990, *System for high-level production in Escherichia coli and rapid purification of recombinant proteins*, Immunol. Methods 4:121).

Accordingly, in another aspect, the present invention relates to a host cell which contains such a vector. Preferably, the host cell is *Escherichia coli*.

In another aspect the present invention relates to a process for preparing the DNA polymerase according to the invention, characterised in that (a) host cells as described above are cultivated in a suitable medium; and (b) the polypeptide formed is isolated from the medium or from the host cells.

In another aspect the present invention relates to a polypeptide which can be prepared by expression of a DNA molecule according to the invention. In particular this is a polypeptide with a 5'-3'-DNA polymerase activity, preferably additionally with a 3'-5'-exonuclease activity.

The present invention also relates to a polypeptide which has a DNA polymerase activity, preferably a 5'-3'-DNA polymerase activity, and contains a sequence which constitutes a cohesive fragment of at least 100 amino acids, preferably at least 200 amino acids of the sequence SEQ ID NO: 2. A particularly preferred polypeptide is one with the sequence SEQ ID NO: 2 or a polypeptide which contains the sequence SEQ ID NO: 2.

The thermostable DNA polymerase according to the invention may advantageously be used for the polymerisation of nucleic acid, particularly by polymerase chain reaction (PCR). It is highly thermostable, efficient and as a result of its proofreading activity has only a very small error content. Methods of polymerising nucleic acid by matrix-dependent polymerisation of nucleotides using DNA polymerases as catalysts, particularly polymerase chain reaction, are known in the art (cf. e.g. Sambrook et al., Molecular Cloning, $2^{nd}$ Ed., Cold Spring Harbour 1989, particularly Chapter 14).

In another aspect the present invention relates to a kit for use in the polymerisation of nucleic acid, containing in separate containers
 (a) a polypeptide of the present invention; and
 (b) a reaction buffer for the polymerisation reaction.

Optionally a kit of this kind may additionally contain dATP, dGTP, dCTP, and dTTP, either as a mixture or in individual containers.

EXAMPLES

Example 1

Culture of *Thermococcus pacificus* and Isolation of Genomic DNA

The organism DSM No. 10394 was cultivated using a ready-made medium made by Messrs Becton Dickinson (Bacto Marine Broth 2216). The medium was prepared in accordance with the manufacturer's instructions and according to the DSMZ (Media 514 and 760) without the use of sulphur. The medium was made anaerobic by the use of $N_2$; this could be checked by the addition of resazurin (1 mg/l final concentration).

First, preliminary cultures were prepared. For this, 2 ml of the starting culture obtained from the DSMZ (DSM 10394) were inoculated onto 20 ml medium under anaerobic conditions. The culture was incubated overnight at 85° C. without agitation in culture flasks with an airtight seal. To start up the main cultures 20 ml of the preliminary culture were anaerobically inoculated onto 500 ml of fresh medium and incubated under the same conditions as the preliminary cultures.

The cultures were harvested by transferring them into anaerobic centrifuge cups and then centrifuging the samples for 15 min at 4° C. and 4000×g. The cell pellet thus obtained was then used for the preparation of the genomic DNA using a commercially obtainable purification kit (Qiagen Genomic-tip System, Qiagen GmbH, Hilden, Germany) in accordance with the manufacturer's instructions.

Example 2

Preparation of a Polymerase Expression Vector

The expression vector was prepared by generally known molecular-biological methods. The polymerase gene was isolated from the genomic DNA of the organism *Thermococcus pacificus* by polymerase chain reaction (PCR). The primers used for this contained, in addition to the sequences homologous to the polymerase gene, a non-complementary nucleic acid sequence which coded for a restriction cutting site, so that by restricting the amplified material and the expression vector the amplified material can be cloned into the expression vector. Oligonucleotides were obtained from Life Technologies GmbH, Karlsruhe, Germany. Other reagents for carrying out the polymerase chain reaction such as Taq DNA polymerase were obtained from QIAGEN GmbH, Hilden, Germany. The coding polymerase gene sequence SEQ ID NO: 1 was amplified using 2.5 units Taq DNA polymerase or the proofreading DNA polymerase Pfu DNA polymerase (Stratagene, Heidelberg, Germany). Also added to the reaction were oligonucleotides (0.2-1.0 µM) as primer, 200 µM of each dNTP and 1× reaction buffer of the corresponding polymerase. A 3-step PCR programme consisting of a denaturing step for melting the starting nucleic acid at about 94° C., a step of annealing of the oligonucleotides to their complementary DNA sequence at about 50-68° C. and an extension step at about 72° C. for amplification was carried out. Depending on the amount of starting nucleic acid, 30 to 40 amplification cycles were carried out. After the PCR reaction the reaction product was examined on an agarose gel by comparison with a suitable DNA size marker to determine its specific length. PCR products of the expected size were either purified directly from the gel or from the PCR reaction. Commercially obtainable systems were used for this (QIAquick PCR Purification Kit or QIAquick gel Purification Kit, QIAGEN GmbH, Hilden, Germany). Purified PCR product and vector-DNA were cut with the corresponding restriction enzymes and the reaction products were again purified as described above. The vector-DNA used was the plasmid pQE80 (QIAGEN GmbH, Hilden), which after the insertion of the target gene is able to express a fusion protein from a so-called His tag and the target protein. In the subsequent ligation reaction equimolar amounts of vector-DNA and PCR product were used and ligated using T4-ligase (Life Technologies GmbH, Karlsruhe, Germany), the corresponding reaction buffer and ATP overnight in a final volume of 20 µl at about 16° C.

Example 3

Preparation of a Bacterial Cell Expressing *Thermococcus pacificus* DNA Polymerase 1 to 2 µl of the ligation reaction were transformed into calcium-competent DH5α-bacterial cells which optionally additionally contained the plasmid pRep4 (QIAGEN GmbH, Hilden). Some of the transformation reaction was then plated out on an agar plate which contained the antibiotic ampicillin and kanamycin or ampicillin on its own as selection marker. The plates were incubated overnight for about 15 to 18 hours at 37° C. Then colonies of bacteria were picked up using sterile toothpicks or pipette tips, transferred into about 3 ml of LB-medium with the appropriate antibiotic and incubated overnight at 37° C. Plasmids were isolated the next day according to the manufacturer's instructions with commercially obtainable kits such as the QIAprep Mini Kit or the QIAGEN Plasmid Tips (QIAGEN GmbH, Hilden, Germany). Plasmids were then checked using suitable restriction enzymes and sequencing to see whether they contained the polymerase gene.

Example 4

Expression and Purification of the DNA Polymerase of *Thermococcus pacificus*

A construct which contained the error-free nucleic acid sequence of the DNA polymerase was transformed into DH5α/pRep4 competent cells. Cells were cultivated in the presence of ampicillin and kanamycin in NZ-amine medium and the expression of the polymerase gene was induced by the addition of IPTG. After the bacterial cells had been harvested, they were lysed using lysozyme, ultrasound and brief decoction. The polymerase protein with a His tag was selectively purified using a commercially obtainable purification kit (QIAexpress protein Purification System, QIAGEN GmbH, Hilden, Germany) according to the manufacturer's instructions by metal affinity chromatography with nickel-NTA-agarose. The protein eluted with imidazole was dialysed against a storage buffer which consisted of 20 mM TrisHCl (pH 8 at 20° C.), 100 mM KCl, 1 mM EDTA, 0.5% (v/v) Nonidet P-40 substitute, 0.5% (v/v) Tween 20 and 50% (v/v) glycerol. The polymerase was stored in this buffer at −20° C.

Example 5

5'-3' Polymerase Activity of *Thermococcus pacificus* DNA Polymerase

To demonstrate that the cloned nucleic acid sequence codes for a DNA polymerase, a test was carried out to check for DNA polymerase activity. The assay shows the extension of an oligonucleotide which is hybridised to single-stranded M13-DNA. If the primer is extended, which can only be done if the protein preparation added has a DNA polymerase activity, a double-stranded DNA molecule is formed from the single-stranded starting nucleic acid. The activity is then detected on an agarose gel by means of a difference in migration of the double-stranded DNA compared with the single-stranded starting DNA. The extension rate is dependent on the polymerase used. The quantity of end product of double-stranded DNA is dependent on the amount of DNA polymerase, the polymerase-specific extension rate and the time taken to carry out the reaction.

All the polymerisation reactions contained 50 ng of M13 mp18-DNA (20 fmol; 7250 bases), 0.1 µM 30-mer oligonucleotide of the sequence 5'-TTTCCCAGTCACGACGT-TGTAAAACGACGG-3' (SEQ ID NO: 5) and 50 µM of each dNTP in 10 µl of 10 mM TrisHCl. Polymerisation reactions contained different amounts of Taq DNA polymerase (0.2, 0.1, 0.05 and 0.01 units; QIAGEN GmbH, Hilden, Germany) or the polymerase preparation to be tested in various dilutions. The reaction was carried out for both enzymes in 1× reaction buffer of Taq DNA polymerase (QIAGEN GmbH, Hilden), to which 1 µg/ml BSA was added, in order to saturate any non-specific protein binding sites on the surface of the reaction vessel.

The polymerisation reaction was carried out in a model PTC-200 Thermocycler made by MJ Research (Biozym, Hess. Oldendorf, Germany). The reaction conditions were chosen as follows: 1 sec denaturing to dissolve any secondary structures present in the DNA, 30 sec hybridisation of the oligonucleotide at 55° C., followed by the primer extension at 72° C. for 3 min.

After the reactions had ended the reaction products were mixed with 1 µl of gel loading buffer (50% glycerol, 1× TAE buffer, 0.02 mg/ml bromophenol blue) and applied to a 1% agarose gel which contained 0.5 µg/ml ethidium bromide to stain the DNA. The gel was analysed at 80 mA for about 15 min in 1× TAE buffer, to separate the single-stranded and double-stranded DNA. The results show that the protein preparation obtained after the expression of the SEQ ID NO:1 has a DNA-dependent DNA polymerase activity.

Example 6

Heat Stability of *Thermococcus pacificus* DNA Polymerase

Figure 1:
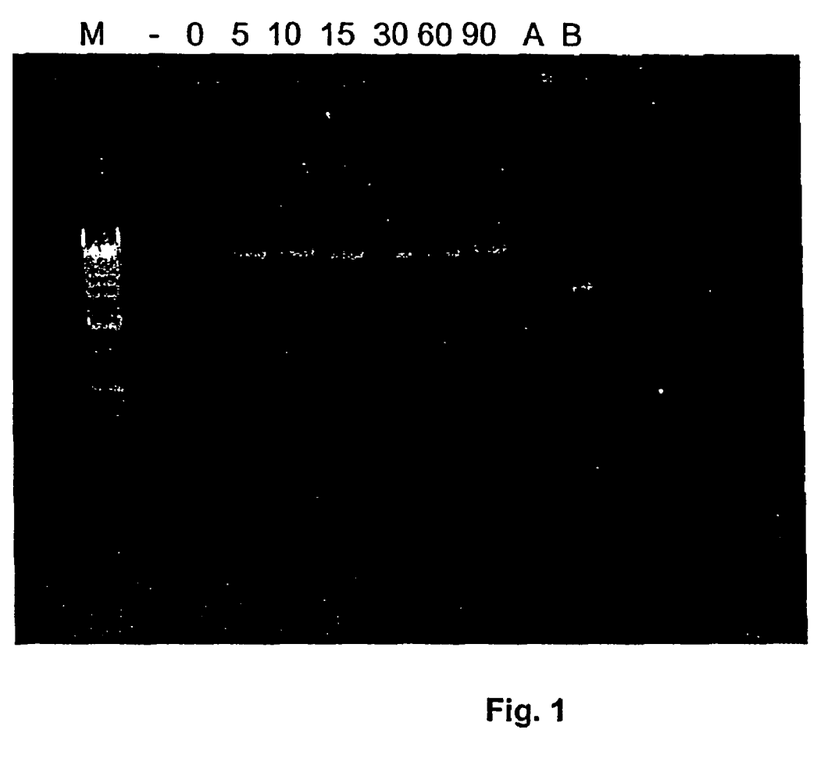
FIG. 1: Heat stability of *Thermococcus pacificus* DNA polymerase. Cf. Example 6. M: marker; –: empty trace; 0-90: preincubation of the polymerase for 0, 5, 10 etc. minutes at 95° C.; A, B: M13 DNA single strand controls with no added polymerase.

The heat stability of the polymerase was examined using the primer extension test described in Example 6. For this purpose, as a modification of the assay described above, 1 unit of the polymerase preparation was preincubated for different lengths of time at 95° C. (0 min, 5 min, 10 min, 15 min, 30 min, 60 min and 90 min). Then the assay was carried out as described in Example 5 with these differently pretreated polymerase preparations. In a modification of the assays described in Example 5 the buffer of Pfu DNA polymerase (Stratagene, Heidelberg) was used as the 1× reaction buffer. The results are shown in FIG. 1. Two control reactions which contained no DNA polymerase were also carried out. The results clearly show that the polymerase shows absolutely no loss of activity even after 90 min incubation, i.e. it has extremely high heat stability (as a comparison: Taq DNA polymerase loses about 50% of the polymerase activity after 60 min incubation at 94° C.).

Example 7

Detection of the 3'-5' Exonuclease Activity of *Thermococcus pacificus* DNA Polymerase The test described as follows was intended to examine to what extent the *Thermococcus pacificus* DNA polymerase has a 3'-5' exonuclease activity. The error rate with which a DNA polymerase duplicates the parent DNA during the replication of the chromosomal DNA is dependent on a number of factors: on the one hand, the choice of base complementary to the starting nucleic acid is crucial, as well as the extent to which a wrongly incorporated nucleotide can have another nucleotide of the polymerase attached to it, and how much 3'-5' exonuclease activity the polymerase has. Using this exonuclease activity, wrongly incorporated nucleotides can be hydrolytically cleaved, so that a nucleotide incorporated by mistake can be replaced by the correct complementary nucleotide. This enzyme activity is also known as the proofreading ability of a polymerase.

Figure 2:
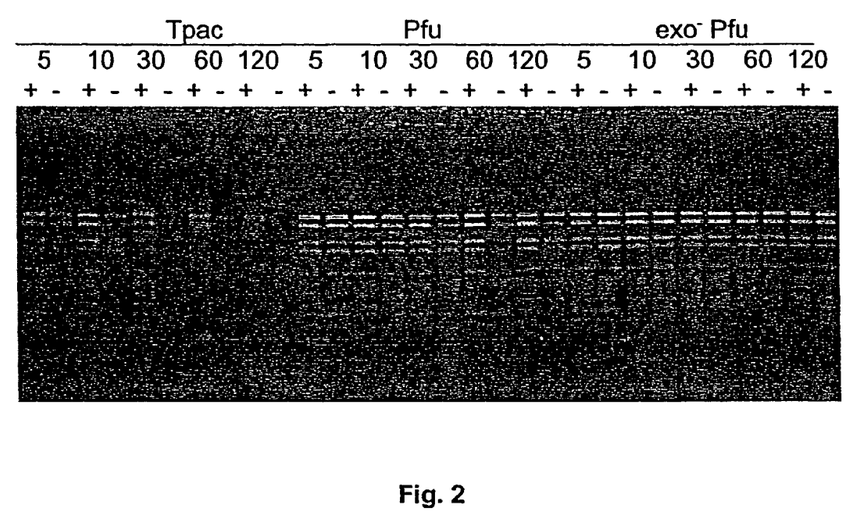
FIG. 2: Detecting the 3'-5' exonuclease activity of *Thermococcus pacificus* DNA polymerase. Cf. Example 7. Tpac: *Thermococcus pacificus* polymerase; Pfu: *Pyrococcus furiosus* polymerase; exo⁻ Pfu: *Pyrococcus furiosus* polymerase the 3'-5' exonuclease of which is mutated so that there is no detectable exonuclease activity; +: addition of dNTPs; –: reaction mixture without dNTPs; 5, 10 . . . : incubation period in minutes.

The 3'-5' exonuclease activity is detected by means of the hydrolytic breakdown of a DNA. For this purpose the following substances were mixed together: 1 µg DNA size marker VI (Roche Biochemicals), optionally 200 µM of each dNTP, 1× Pfu DNA polymerase reaction buffer (Stratagene, Heidelberg) and 1 unit of *Thermococcus pacificus* DNA polymerase. Reactions were set up with and without nucleotides: in the absence of nucleotides the exonuclease activity is predominant, whereas it is inhibited by the addition of dNTPs. As a positive control, 1 unit of Pfu DNA polymerase was used (Stratagene, Heidelberg), having a 3'-5' exonuclease activity, while the negative control used was Pfu Exo minus DNA polymerase (Stratagene, Heidelberg), the exonuclease activity of which is sharply reduced by point mutagenesis. The reactions were incubated for different periods (5 min, 10 min, 30 min, 60 min and 90 min) at 72° C. and then analysed on a 1% agarose gel. The results shown in FIG. 2 clearly demonstrate that the *Thermococcus pacificus* DNA polymerase has a 3'-5' exonuclease activity many times greater than that of Pfu DNA polymerase.

Example 8

Detecting the Proofreading Ability of *Thermococcus pacificus* DNA Polymerase Under PCR Conditions Extremely thermostable DNA polymerases with proofreading ability are used in particular in PCR reactions which are intended for the preparation of mutation-free DNA fragments. This is particularly important for certain molecular-biological applications such as the cloning of error-free PCR fragments for protein expression. DNA polymerases which have a 3'-5' exonuclease activity synthesise PCR products with an error rate up to 12 times lower than Taq DNA polymerase, the standard enzyme for PCR applications.

Figure 3:
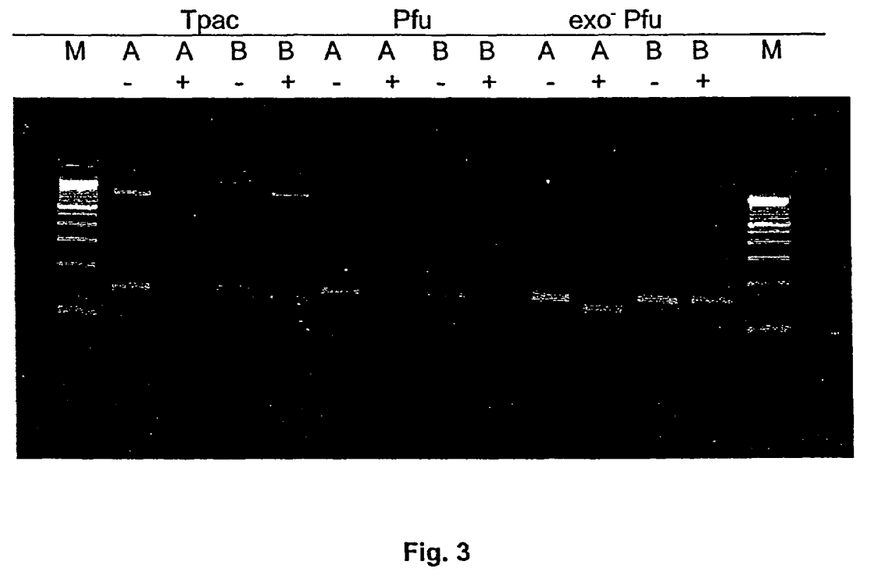
FIG. 3: Detection of the proofreading ability of *Thermococcus pacificus* DNA polymerase under PCR conditions. Cf. Example 8. Tpac: *Thermococcus pacificus* polymerase; Pfu: *Pyrococcus furiosus* polymerase; exo⁻ Pfu: *Pyrococcus furiosus* polymerase, the 3'-5' exonuclease of which is mutated so that there is no detectable exonuclease activity; A, B: characterise 2 independent PCR reactions; M: marker; +: digestion with BamHI takes place; –: undigested PCR fragment.

In the present test the ability of *Thermococcus pacificus* DNA polymerase to correct errors under PCR conditions in a mismatch repair assay was tested. This assay was developed specially for this purpose (U.S. Pat. No. 5,491,086) and comprises an amplification step and a diagnostic restriction digestion. For the PCR reaction either primers (wild-type primers) are used which are totally homologous to the target DNA sequence (Taq DNA polymerase genes) and the 151 bp long PCR product of which can be cleaved by the BamHI restriction enzyme, thereby generating a DNA fragment 132 bp and 19 bp in size. Parallel to this, reactions were carried out, the primer molecules of which have a base mismatch at the 3' end. If the incorrect base is not corrected during the PCR, the BamHI cutting site is destroyed and the PCR product cannot be cleaved in a restriction digestion with the enzyme BamHI. If on the other hand the polymerase is capable of recognising wrongly paired bases and hydrolytically removing them, the correct complementary base can be incorporated and the PCR product yields the two expected DNA fragments after restriction digestion. The wild-type primers used have the sequences: 5'-GCACCCCGCTTGGGCAGAG-3' (SEQ ID NO: 6) and 5'-TCCCGCCCCTCCTGGAAGAC-3' (SEQ ID NO: 7). Alternatively, primers were used the 3' ends of which had a C:A, C:T or C:C mismatch. PCR reactions were carried out with the *Thermococcus pacificus* DNA polymerase, Pfu DNA polymerase (Stratagene, Heidelberg, Germany), which has a mismatch correction, and Pfu Exo minus DNA polymerase (Stratagene, Heidelberg, Germany), which cannot perform this error correction. PCR reactions contained 20 ng of plasmid pQE-31 (Qiagen GmbH, Hilden, Germany), which contained the Taq DNA polymerase gene target sequence, 1 unit of the appropriate DNA polymerase, 1× Pfu reaction buffer, 200 µM of each dNTP and 1.5 µM of each primer. The final volume of the reaction was 50 µl. The PCR reactions were carried out in an MJ Research PTC-200 Thermocycler (Biozym, Hess. Oldendorf, Germany). The PCR programme comprised an initial 1 min denaturing step at 94° C., a 30 sec denaturing step at 94° C., a hybridisation step at 62° C. and an extension step at 72° C. for 1 min. PCR products were purified with the QIAquick PCR Purification Kit (QIAGEN GmbH, Hilden, Germany). Identical amounts of PCR product were digested per 100 ng of PCR product with one unit of BamHI for 90 min at 37° C. Then the PCR products thus treated were analysed on a 4% Metaphor Agarose gel (Biozym, Hess. Oldendorf, Germany). The results are shown in FIG. 3. The results show that, as expected, the Pfu Exo minus DNA polymerase is unable to repair the mismatch, i.e. the PCR product produced with mutated primers cannot be cleaved by the restriction enzyme BamHI. By contrast the non-mutated Pfu DNA polymerase is capable of correcting the base mismatch. The *Thermococcus pacificus* DNA polymerase is capable on the one hand of synthesising the desired PCR product under PCR conditions, and can also recognise mismatched bases under PCR conditions, remove them hydrolytically and replace them with the correct complementary nucleotide. Thus, it is clear that *Thermococcus pacificus* DNA polymerase is suitable for carrying out so-called High Fidelity PCR reactions.

The invention claimed is:

1. An isolated polypeptide having 5'-3'-DNA polymerase activity, which polypeptide is encoded by a DNA molecule, wherein said DNA molecule is
the sequence of SEQ ID NO: 1,
wherein said polypeptide further exhibits 3'-5' exonuclease activity.

2. A kit for use in the polymerization of nucleic acid, said kit comprising:
(a) a polypeptide according to claim 1; and
(b) a reaction buffer for the polymerization reaction; and optionally
(c) dATP, dGTP, dCTP, and dTTP, either as a mixture or in individual containers.

* * * * *